United States Patent [19]

Adobbati

[11] Patent Number: 5,458,599
[45] Date of Patent: Oct. 17, 1995

[54] SYSTEM FOR THE USE IN THE FIXATION OF A FRACTURED BONE

[76] Inventor: Ricardo N. Adobbati, 615 Palo Verde, Brownsville, Tex. 78520

[21] Appl. No.: 230,639

[22] Filed: Apr. 21, 1994

[51] Int. Cl.[6] .............................. A61B 17/62; A61B 17/72
[52] U.S. Cl. ................ 606/56; 606/54; 606/63; 606/68
[58] Field of Search .................. 606/54, 56, 60, 606/62, 63, 67, 68

[56] References Cited

U.S. PATENT DOCUMENTS

| | | |
|---|---|---|
| 3,659,257 | 9/1973 | Fischer et al. . |
| 3,760,802 | 9/1973 | Fischer et al. . |
| 4,091,806 | 5/1978 | Aginsky . |
| 4,204,531 | 5/1980 | Aginsky . |
| 4,227,518 | 10/1980 | Aginsky . |
| 4,453,539 | 6/1984 | Raftopoulos et al. . |
| 4,624,249 | 11/1986 | Alvarez Cambras ................ 606/54 |
| 4,768,524 | 9/1988 | Hardy ................................... 606/54 |
| 5,003,969 | 4/1991 | Azer et al. ........................... 606/54 |
| 5,057,103 | 10/1991 | Davis ................................... 606/63 |

*Primary Examiner*—Tamara L. Graysay
*Assistant Examiner*—Scott B. Markow
*Attorney, Agent, or Firm*—Gunn, Lee & Miller

[57] ABSTRACT

The present invention discloses a bone fixation device composed of two separate connectable sections: a compression device and an elongated member. The compression device is further composed of four interacting elements: a hollow, elongated body; a flexible compression wire; at least two compression blades and a hollow cylinder. The elongated member may be adapted to accept shims. The present invention also discloses a bone alignment device composed of: two adjustable circular members; a tubular, longitudinally extending member connecting the two circular members; at least two longitudinally extending connectors also connecting the two circular members and at least one adjustable bone alignment means attached to each connector for applying pressure to the limb containing the fractured bone. The present invention also discloses a system for using the bone alignment device and bone fixation device of the present invention together to align and fix a broken bone.

22 Claims, 12 Drawing Sheets

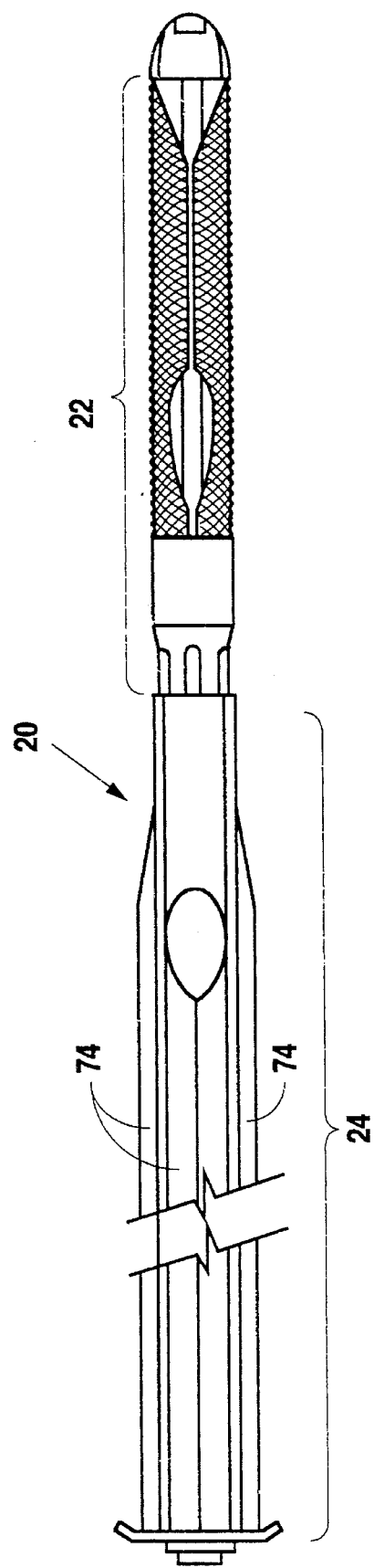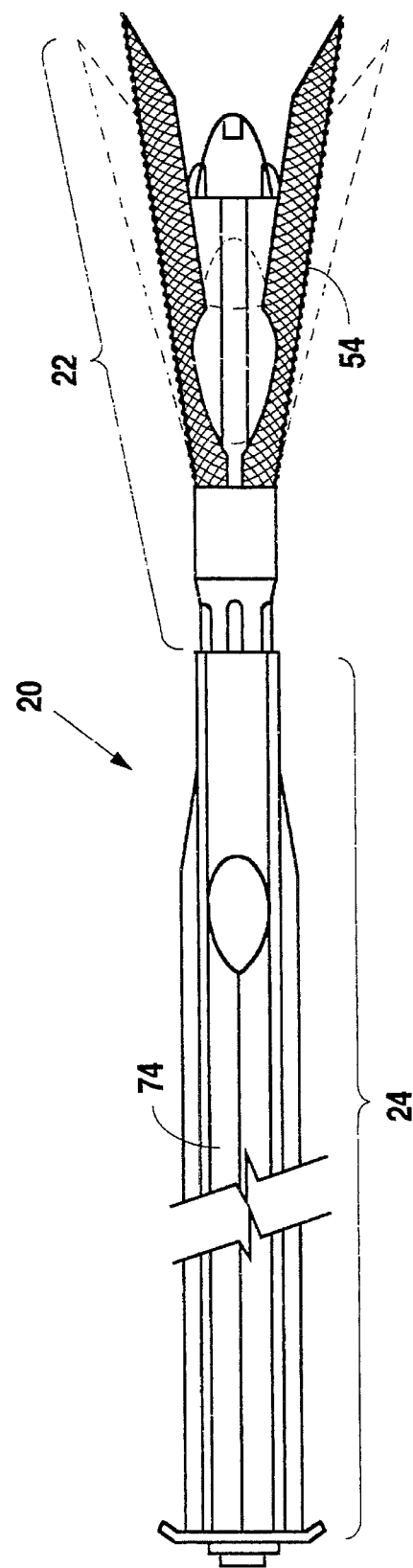

SYSTEM FOR THE USE IN THE FIXATION OF A FRACTURED BONE

BACKGROUND OF THE INVENTION

The present invention relates generally to the field of art of bone fixation devices, also known as intramedullary devices, which are inserted into the medullary canal of a fractured bone to promote the healing of the fractured bone and to facilitate the functional rehabilitation of the fractured bone.

The present invention also relates to the field of devices which are used to align the broken bone.

The present invention further relates to a system used in the operating room by a surgeon and the assisting medical personnel which allows the fractured bone to be aligned with a reduced risk of exposure to radiation and then fixed.

When a bone is broken, the surgeon aligns the bone manually with the aid of imaging equipment, such as, a fluoroscope and then immobilizes the various bone segments using one or more rigid devices that span the fracture site. These devices are located either externally to the body, internally on the exterior of the bone cortex or internally in the medullary canal of the bone.

The external devices are generally exterior frames which enter the body and attach to the bone by metal pins, such as a Hoffman device or a Brooker frame. The disadvantages of these devices are the difficulties in manipulating the devices to achieve the desired compressive force required to unite the bone segments, the inadvertent manipulation after the devices are set in the desired position and the increased chance of infection along the metal pins penetrating the skin and underlying tissue.

The internal devices which contact the exterior of the bone cortex are cortical plates. These plates are implanted surgically and attached to the bone cortex by screws. Cortical plates can apply compression to the bone segments but have many disadvantages; such as, the danger of damaging vital structures by extensive dissection of muscle and periosteum, the increased possibility of infection and the increased chances of necrosis and non-union of the bone fragments by decreased blood supply to the fragments.

The internal devices which are located in the medullary canal are intramedullary nails or devices which are surgically implanted into the medullary canal. These devices minimize soft tissue dissection and destruction and reduce the chances of infection. However, the earliest types of these devices were too small in diameter to facilitate rehabilitation or too large in diameter resulting in a weakened bone shaft and reduction in the blood supply to the end of the fractured bone as a result of enlarging the medullary cavity. Further, these prior art intramedullary nails provided limited lateral support by only contacting the inner wall of the medullary cavity of the bone over a small region. Additionally none of them provided a compression force along the length of the bone.

Later improved intramedullary devices did increase lateral support of the fractured bone by using an intramedullary device having an expandable end portion. However, these devices sometimes included complex mechanisms to effect the expansion and these devices were relatively expensive. U.S. Pat. Nos. 3,760,802 and 4,453,539 are examples of these devices.

A more recent intramedullary device is disclosed in U.S. Pat. No. 5,057,103, which allegedly provides compressive force along the length of the bone to close the fracture and promote healing. This intramedullary nail has a straight, non-flexible cylindrically shaped outer member and a cylindrically shaped inner member which fits into the outer member. The inner member has hinged arms for engaging the interior of the bone cortex in the distal bone segment and is moved from stowed position to deployed position by sliding the inner member toward the outer member in a distal direction. A U-shaped member for engaging the cortex on the proximal bone segment is also present. The arms of this intramedullary nail are only 0.174 inches wide and 0.078 inches thick. From FIG. 1 of this patent, it can be seen that the arms engage the bone cortex in the metaphysis of the bone. The compression force that is applied to the bone results from adjusting this force across the fracture site with the arms and U-shaped member.

The bone fixation device of the present invention is an intramedullary nail which also provides a compression force to the bone; however, the configuration of the bone fixation device of the present invention is considerably different than that of the device disclosed in U.S. Pat. No. 5,057,103. In addition to providing a compression force to the bone, the present invention provides additional advantages over the device disclosed in U.S. Pat. No. 5,057,103 as well as all of the prior art intramedullary nails.

The present invention also provides a device which aligns the broken bone and holds it in the aligned position while the bone fixation device is being inserted into the medullary canal. This bone alignment manipulation has heretofore been performed using the hands of the surgeon or the hands of the assisting medical personnel while monitoring the progress with a fluoroscope or some other comparable imaging apparatus. Even though the medical personnel use lead aprons and barriers over the trunk of the body as protection against the radiation, the hands and arms of the personnel are exposed to frequent doses of radiation during the same operation. Thus, there is a need to provide a device which can align and hold the aligned broken bone in place while the intramedullary device is being inserted.

The present invention also discloses a system for use in the operating room to fix a broken bone where the broken bone is aligned with the bone alignment device of the present invention and then fixed with the bone fixation device of the present invention. The present invention provides an improved system for fixing broken bones by reducing the risk of overexposure to radiation by medical personnel and by providing an improved intramedullary bone fixation device with several features to apply compressive force to the fractured bone and which allows adjustment and replacement of portions of the device while the remaining portion of the device is still inserted in the intramedullary canal.

SUMMARY OF THE INVENTION

The present invention provides a bone fixation device which applies compressive force over the longitudinal axis of the bone.

The present invention further provides a bone fixation device which comprises two distinct pieces which are connected but which can be separated with replacement of the proximal portion to obtain a better fit. This adjustment can occur while the distal portion of the device remains in the distal portion of the medullary canal of the bone.

The present invention also provides a bone fixation device which allows the fracture to be compressed in two ways by two different elements of the device if such adjustment is necessary.

The present invention further provides a bone fixation device which can be made larger for a better fit without the danger of breaking the bone or without the need for reaming the medullary canal thus preserving the endosteal circulation.

The present invention additionally provides a bone fixation device which will not rotate in the medullary canal.

The present invention further provides a bone fixation device which is flexible so that it adapts to the shape of the bone.

The present invention additionally provides a bone alignment device which allows the surgeon and assisting medical personnel to align the fractured bone without directly using their hands and thus protecting them from overexposure to radiation.

The present invention also provides a system for use in the fixation of a fractured bone comprising the bone alignment device and the bone fixation device.

The present invention discloses a bone fixation device composed of two separate connectable sections: a compression device and an elongated member. The compression device is basically composed of four interacting elements: a hollow, elongated body; a flexible compression wire; at least two compression blades; and a hollow cylinder. The elongated member may be adapted to accept shims.

The present invention also discloses a bone alignment device composed of: two adjustable circular members; a tubular, longitudinally extending member connecting the two circular members; at least two longitudinally extending connectors also connecting the two circular members; and at least one adjustable bone alignment means attached to each connector for applying pressure to the limb containing the fractured bone.

The present invention also discloses a system for using the bone alignment device and bone fixation device of the present invention together to align and fix a broken bone.

BRIEF DESCRIPTION OF THE DRAWINGS

FIGS. 1a and 1b are side elevational views of the bone fixation device of the present invention. In FIG. 1a the compression blades are in the closed position and in FIG. 1b the compression blades are in the open position with the dotted lines showing the fully opened position.

DETAILED DESCRIPTION OF THE PREFERRED EMBODIMENT

Figure 2:
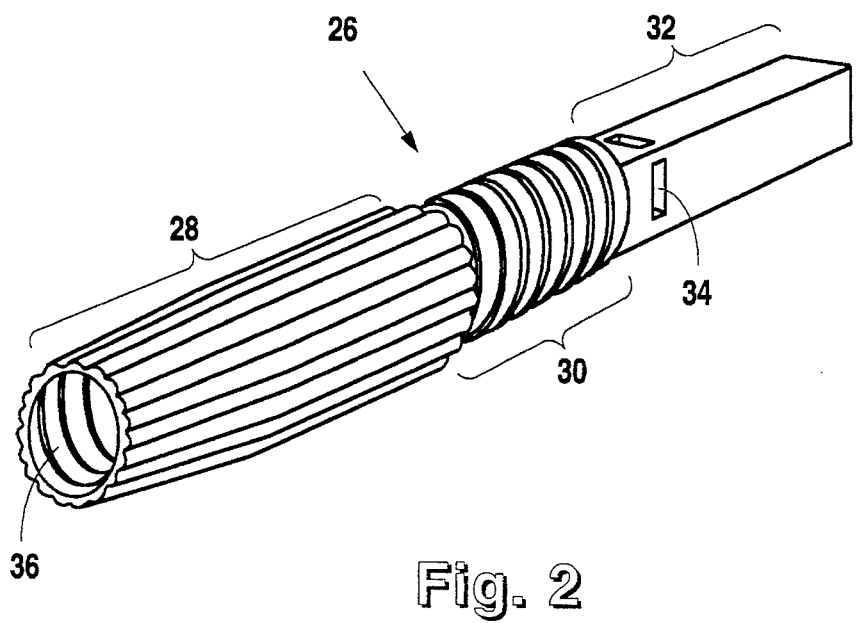
FIG. 2 is a perspective view of the preferred hollow elongated body of the bone fixation device of the present invention.
Figure 3A:
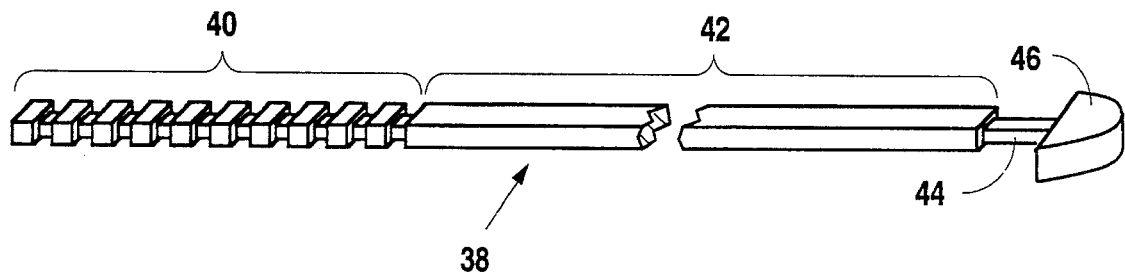
FIGS. 3a–d are perspective views of the compression wire and of the bone fixation device of the present invention.
Figure 3B:
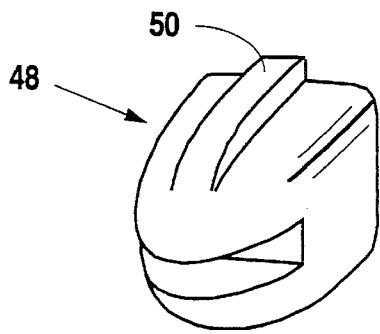
Figure 3C:
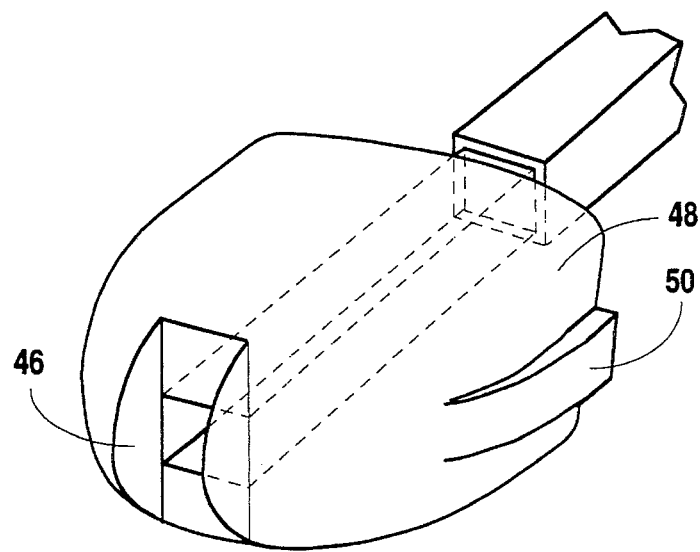
Figure 3D:
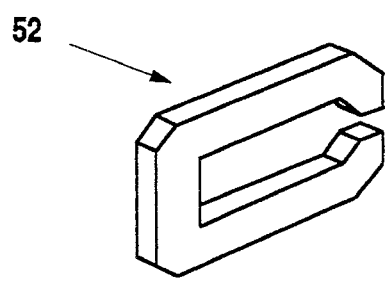
Figure 3E:
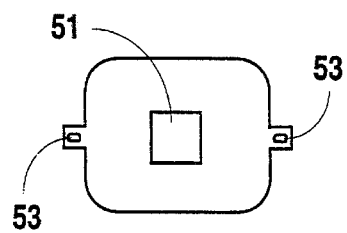
FIG. 3e is a bottom view of the head of the compression wire.

The bone fixation device of the present invention is inserted into the medullary canal of the fractured bone of a patient using a surgical procedure. The bone fixation device is inserted by making an incision in the skin and a small hole with an awl in the end of the bone into which the device is to be inserted.

To provide an orientation for a detailed description of the present invention, the end of the bone into which the device is inserted will be referred to as the proximal end of the bone as will portions of the device which are oriented toward the proximal end of the bone. Likewise, the opposite end of the bone from which the device is inserted will be referred to as the distal end of the bone as will portions of the device which are oriented toward the distal end of the bone.

FIG. 1a shows a side elevational view of the bone fixation device (20) in accordance with the preferred embodiment of the present invention in a closed position. FIG. 1b shows a side elevational view of the bone fixation device (20) in an open position with the compression blades (54) extended. The bone fixation device (20) is inserted into the medullary canal of a fractured bone as a means for fixing and promoting healing of the fractured bone.

The bone fixation device (20) contains two separate connectable sections: a compression device (22) adapted for removable engagement with the hollow elongated member (24) which has an inner surface adapted for removable engagement with the compression device (22). The inner surface of the member (24) is preferably fluted at the distal end to allow the removable engagement of member (24) with the compression device (22). Likewise the outer surface of the compression device (22) is fluted at its proximal end thus allowing removable engagement with the member (24). All of the elements of the bone fixation device (20), which will be described in detail below, are constructed of flexible or semi-rigid biocompatible metals, such as stainless steel, titanium or titanium alloys.

The compression device (22) is made of four distinct sections which are: a hollow, elongated body (26); a flexible compression wire (38); at least two compression blades (54); and a hollow cylinder (62) which are shown in detail in FIGS. 2–8.

The hollow, elongated body (26) has an outer surface with three contiguously connected, distinctly shaped portions positioned in a proximal to distal direction as follows: a first portion, a second portion and a third slotted portion. The outer surface of these portions of the elongated body can have any shape as long as the elements with which they engage are shaped to be compatible with the distinctly shaped portions of the elongated body.

In the preferred embodiment, the distinct shapes of the outer surface of the elongated body (26) are shown in FIG. 2. The elongated body (26) is hollow so that the compression wire (38) can pass through. The outer surface of the first portion (28) is fluted and functions as the means to allow removable engagement of the compression device (22) with the fluted inner surface at the distal end of the elongated member (24). The first portion (28) is cylindrical and tapers at its proximal end to allow this removable engagement. The proximal end of the inner surface (36) of the first portion (28) is threaded to allow a tool to engage this portion of the compression device (22) for its removal when necessary. The outer surface of the second portion (30) is threaded to allow for engagement with a hollow cylinder which secures the arms of the compression blades (54) to hold the compression blades on the elongated body (26). The outer surface of the third portion (32) is square-shaped with slots (34) at its proximal end. The arms of the compression blades (54) are adapted to fit into these slots (34). The inner surface of the third portion (32) is also square-shaped to fit with the square-shaped rod (42) of the compression wire (38).

Referring now to FIGS. 3 a–e, a preferred flexible compression wire (38) is described which is insertable through the elongated body (26) from the proximal end of the first portion. The compression wire (38) as shown in FIG. 3a comprises from proximal to distal ends: a region composed of a series of teeth (40), a square-shaped rod (42), an indentation (44) and an engagement point (46). The engagement point (46) fits into a head (48) shown in FIG. 3b which has two laterally located prongs (50) extending longitudinally from the head (48). Once the head (48) is engaged on the engagement point (46) as shown in FIG. 3c then a securing means, such as a clip (52), as shown in FIG. 3d holds the head (48) in place on the compression wire (38). The square-shaped rod (42) is shaped as such to avoid rotation in the square-shaped third portion (32) of the elongated body (26). The prongs (50) on the head (48) fit into the inner groove of the inner surface of the compression blades (54). FIG. 3e shows the bottom of the head (48) with the opening (51) through which the compression wire (38) extends. The small laterally located openings (53) are situated on the bottom of the prongs (50) and are present to engage the ends (57) of the tips (56) of the compression blades (54) in the closed position as shown in FIG. 1a. The region composed of a series of teeth (40) allows this region to interact with a special instrument to cam up the compression wire (38) and cause the head (48) to slide proximally to open the compression blades (54) and engage the interior of the bone cortex in the distal bone segment. The head (48) can also slide distally to close the compression blades (54) and thus disengage from the interior of the bone cortex. The compression wire (38) can be different sizes depending upon the bone to be fixed.

Figure 4A:
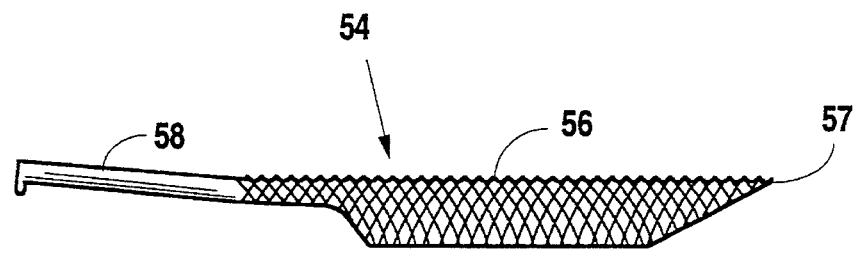
FIGS. 4a–c are side and top elevational views of the compression blades of the bone fixation device of the present invention.
Figure 4B:
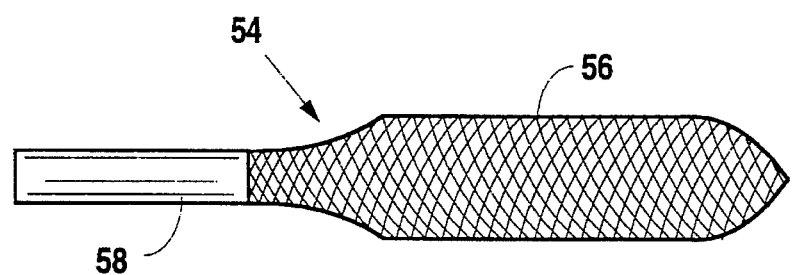
Figure 4C:
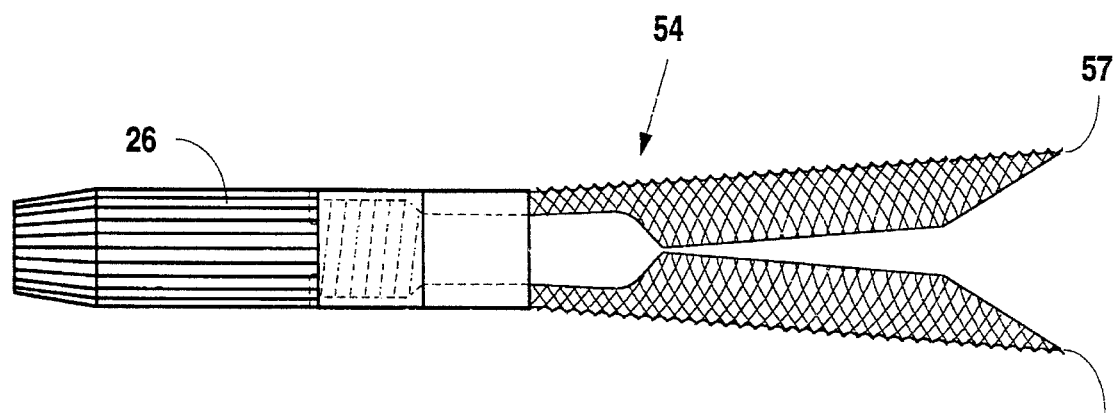
Figure 4D:
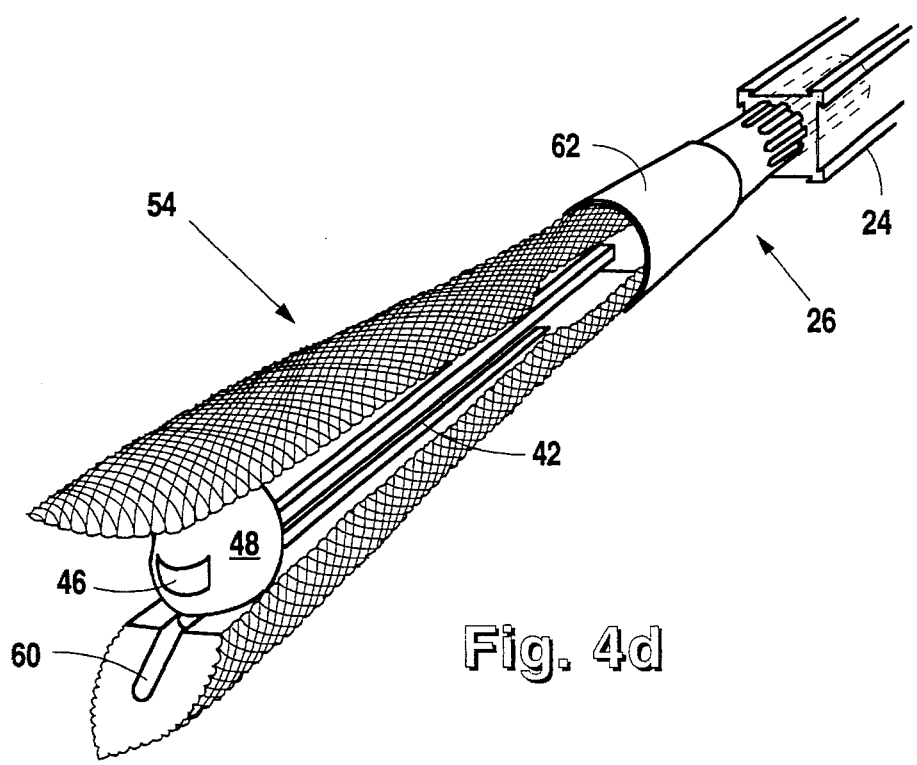
FIG. 4d is a perspective view of the compression blades of the bone fixation device of the present invention.

The compression blades (54) are shown in FIGS. 4a–d. At least two compression blades are used in the present invention but more blades can be used if the third portion (32) of the elongated body (26) has slots (34) to accommodate them. Additionally, when the compression blades are attached to the elongated body (26), their combined shape should be rounded to facilitate the passage of the bone fixation device into the medullary canal. Referring to FIGS. 4a–b, each of the blades (54) should have an arc-shape with a tip (56) with an end (57) at the distal end of the blade (54) and an arm (58) at the proximal end of the blade (54). The arm is adapted to engage one of the slots (34) on the third portion (32) of the elongated body (26). FIG. 4c shows the compression blades (54) attached to the elongated body (26). Referring to FIG. 4d, the compression blade (54) further comprises an inner groove (60) which extends longitudinally on the inner surface of the blade (54). As discussed above, each of the inner grooves (60) is engageable with one of the laterally located prongs (50) on the head (48) allowing the compression wire (38) to slide along the inner groove (60) of the blade (54). The outer surface of the tip (56) of the blade (54) is like a file with a rough and ridged surface. The arms (58) of the blades (54) are flexible and the tip (56) of the blade (54) is rigid. The same material is used to make the entire blade (54); however, the arms (58) are more flexible because the material is thinner than the material in the tip (56). The arm (58) is oriented at an angle so that when the blade (54) is engaged in the slot (34) of the third portion (32) of the elongated body (26), it is angled outwardly several degrees such as 2°–5°, from the elongated body (26) as shown in FIG. 4c. The compression blades are of different sizes to adapt to the size of the medullary canal of the bone in which it will be used.

Figure 5:
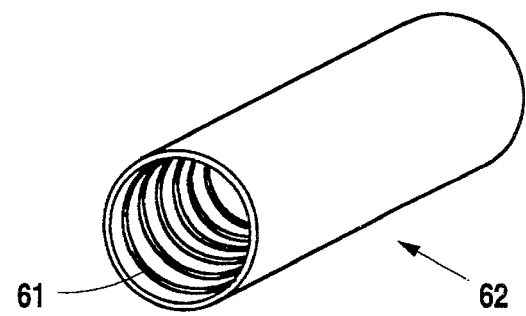
FIG. 5 is a perspective view of the hollow cylinder of the bone fixation device of the present invention.

A hollow cylinder (62) having an inner surface (61) adapted to engage the second portion (30) of the elongated body (26) is shown in FIG. 5. Once the compression blades (54) and the compression wire (38) are engaged with the elongated body (26) then the cylinder (62) can be engaged with the second portion (30) of the elongated body (26) to secure the arms (58) of the blades (54) into the slots (34) on the third portion (32) of the elongated body (26). The first connectable section, the compression device (22), of the bone fixation device (20) has now been assembled.

Figure 6A:
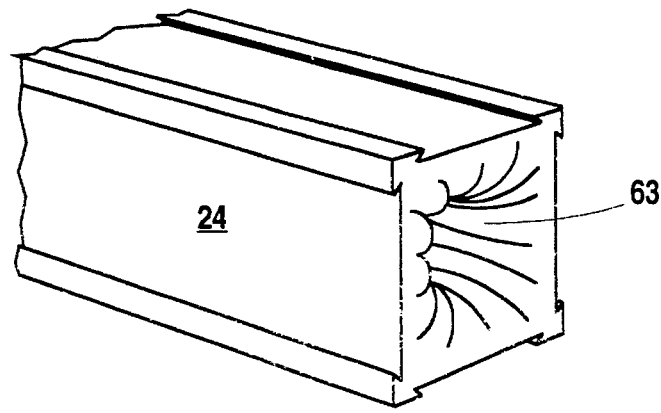
FIGS. 6a–c are perspective views of the elongated member of the bone fixation device of the present invention.
Figure 6B:
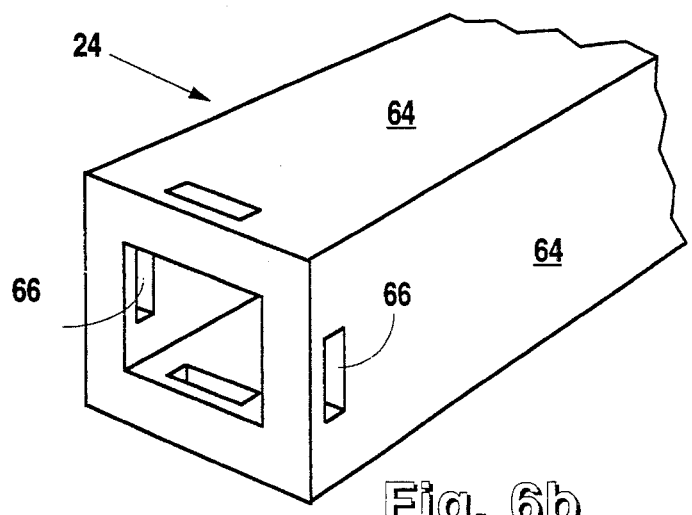
Figure 6C:
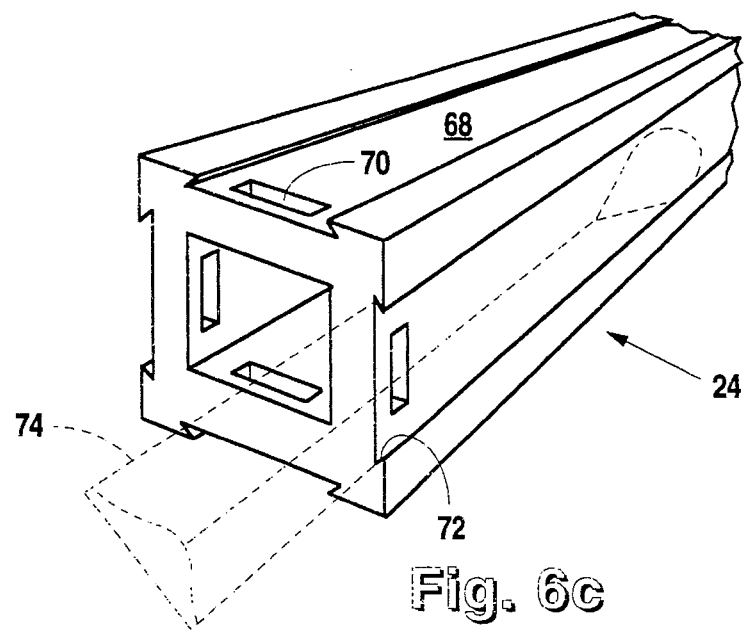

The second connectable section of the bone fixation device (20) of the present invention is a hollow elongated member (24) which is curved in at least substantial conformance with the medullary canal of the fractured bone; such as, the femur, tibia, humerus, radius or ulna. FIGS. 6a–c show the elongated member (24) in more detail. At least the distal end (63) of the inner surface of the elongated member (24) is fluted as shown in FIG. 6a for removable engagement with the compression device (22).

The outer surface of member (24) can have any shape; although it is preferred to use a shape with flat surfaces and corners, such as a triangular shape, square shape, or pentagon shape. A square-shaped outer surface is the most preferred shape. FIGS. 6b and 6c show two configurations of the square-shaped member (24) as viewed from the proximal end. In FIG. 6b each of the sides (64) of the square-shaped outer surface have a slot (66) in the proximal end of the member (24) into which a tool can be engaged for insertion into and removal of the member (24) from the medullary canal or for the insertion into and removal of the bone fixation device (20) from the medullary canal. The square-shape is advantageous because it prevents rotation of the device in the medullary canal as opposed to the prior art cylindrical intramedullary nails. In FIG. 6c, the outer surface of each of the sides (68) of the square-shaped member (24) contains a slot (70) and further contains a set of longitudinally extending parallel grooves (72). This set of parallel grooves (72) on each side (68) of the square-shaped member (24) is present for the engagement of at least one longitudinally extending shim (74).

Figure 7A:
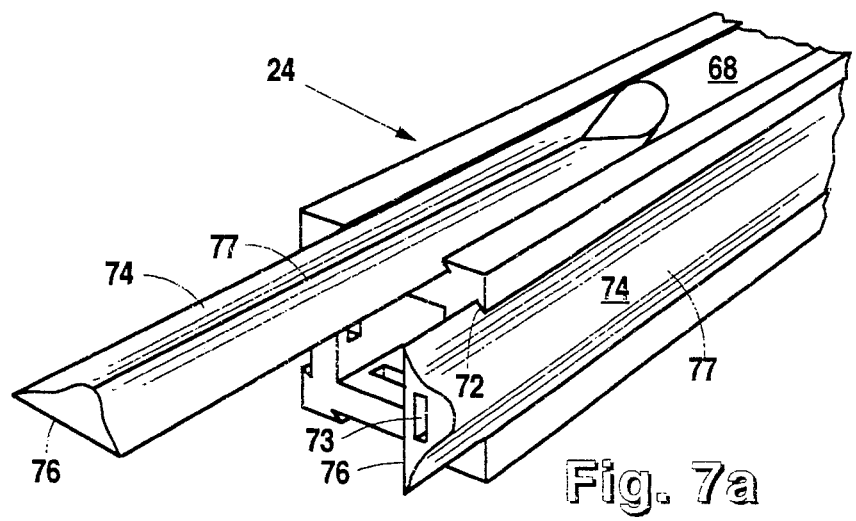
FIG. 7a is a perspective views of the shims of the bone fixation device of the present invention.
Figure 7B:
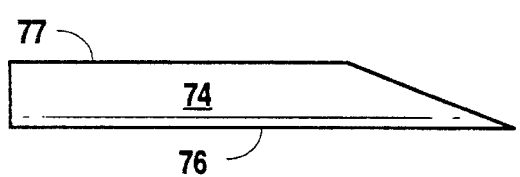
FIG. 7b is a side view of the shim of the bone fixation device of the present invention.
Figure 7C:
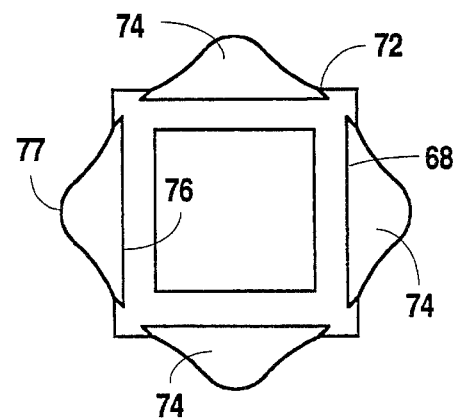
FIG. 7c is a cross-sectional view of the elongated member with shims engaged in the parallel grooves.

FIGS. 7a–c show the shims (74) and how they engage the side (68) of the configuration of member (24) of FIG. 6c via the set of parallel grooves (72). The shim (74) has a flat base (76) for engaging the pair of longitudinally extending parallel grooves (72) on the outer surface of the side (68) of the member (24) and a slot (73) at the proximal end for engagement with a tool for removal and insertion of the shim. The purpose of the shims (74) is to provide an additional means to exert a compressive force on the broken bone. The shims (74) additionally help to align the bone if small alignment adjustments must be made. Further, the shims (74) allow the bone fixation device to fit in the medullary canal snugly and thus not rotate. The shim (74) is wedge-shaped for a portion of the distal end. Approximately two-thirds of the shim (74) at the proximal end is the same thickness from base (76) to the apex (77) and approximately the other one-third of the shim (74) is slanted from this portion toward the distal end. This latter portion is the wedge-shaped portion. The configuration of the elongated member (24) in FIG. 6b does not require the use of any shims. The configuration of the elongated member (24) in FIG. 6c allows from one to four shims to be utilized to achieve enhanced compression, proper alignment and a better fit if necessary. The configuration of the elongated member (24) can be utilized without shims (74). FIG. 7b shows an elevational side view of a shim (74). FIG. 7c shows the elongated member (24) of FIG. 6c with four shims (74) engaged in the set of longitudinally extending parallel grooves (72). Each of the shims (74) can be of a different or the same thickness. The thickness of the shims (74) are used to achieve the desired results as determined by the surgeon using the bone fixation device (20).

Figure 8A:
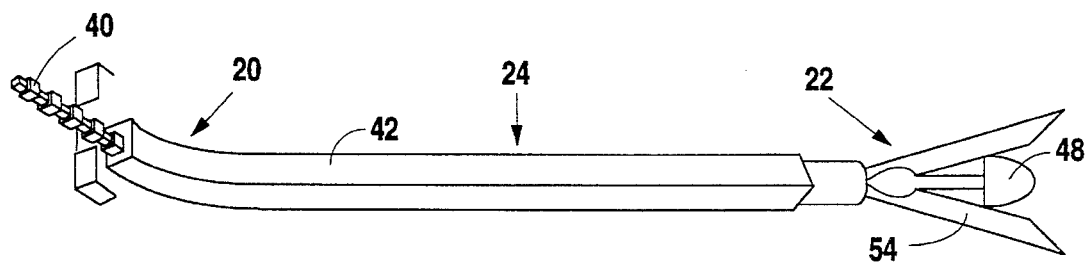
FIG. 8a is a perspective view of the entire bone fixation device of the present invention.
Figure 8B:
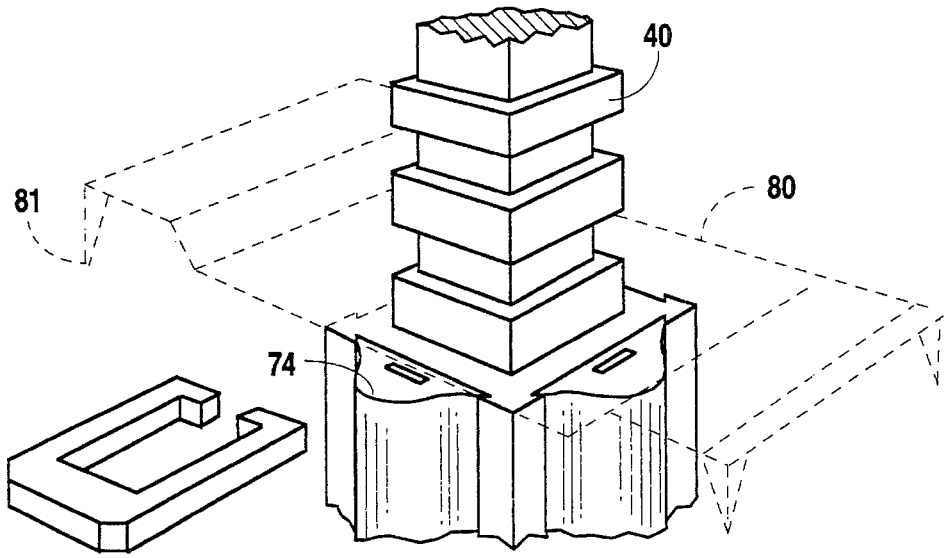
FIG. 8b is a perspective view of the proximal end of the bone fixation device of the present invention with a plate and clip for locking the device after insertion.

The two connectable sections, the compression device (22) and the elongated member (24) of the bone fixation device (20) connect by taking the proximal end of the compression wire (38) which is extending beyond the proximal end of the compression device (22) and inserting it through the elongated member (24). Then the elongated member (24) is removably connected to the compression device (22) by engaging the first portion (28) of the elongated body (26) of the compression device (22) with the distal portion of the inner surface (36) of the elongated member (24). FIGS. 8a shows the bone fixation device (20) after the connection of the compression device (22) and the elongated member (24) with the compression blades (54) in an open position. FIG. 8b shows the proximal end of the bone fixation device (20) with the plate (80) with bone engaging points (81) which is placed on the proximal end of the elongated member (24) after insertion and adjustment of the bone fixation device (20) in the medullary canal of the bone.

The above described bone fixation device (20) is used in a process where the fractured bone must be aligned during the insertion of the bone fixation device (20). Presently, the surgeon and assisting medical personnel use their hands to align the fractured bone while monitoring the progress of these manipulations with a fluoroscope or some other comparable imaging apparatus. Throughout this alignment procedure, numerous X-rays are taken which subject the staff who are manipulating the bone to an increased exposure to radiation. The present invention discloses a device which replaces the hands of the staff for aligning the bone and holding it in the aligned position while the X-rays are taken to monitor the alignment process.

The present invention also discloses a fractured bone alignment device for use in the fixation of a fractured bone by placing the device on the limb of an individual containing a fractured bone. The bone alignment device can be made of any material that is radiolucent, such as preferably aluminum or alternatively carbon fibers. The device is described in detail in FIGS. 9–13.

Figure 9:
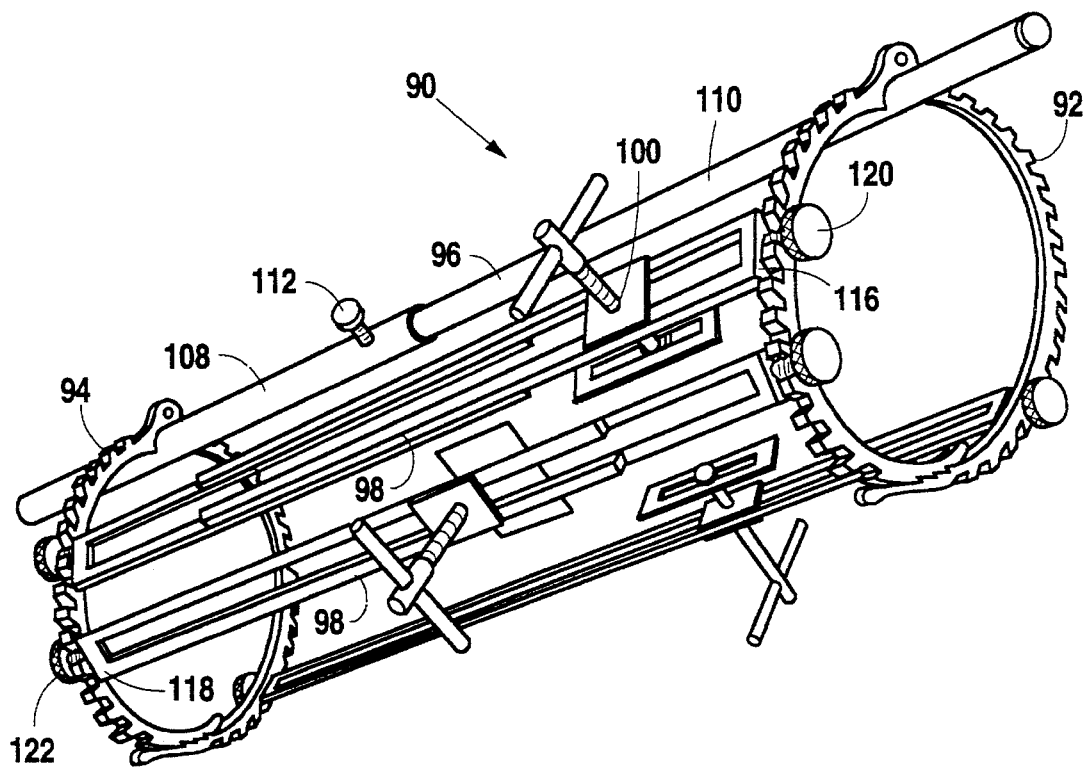
FIG. 9 is a perspective view of the bone alignment device of the present invention.

The bone alignment device (90) is shown in FIG. 9. The alignment device (90) has the following elements: a first circular member (92) and a second circular member (94); a tubular, longitudinally extending member (96); at least two longitudinally extending connectors (98) and at least one adjustable bone alignment means (100) attached to each connector (98) where both the tubular member (96) and the longitudinally extending connectors (98) connect the first (92) and second (94) circular members.

Figure 10A:
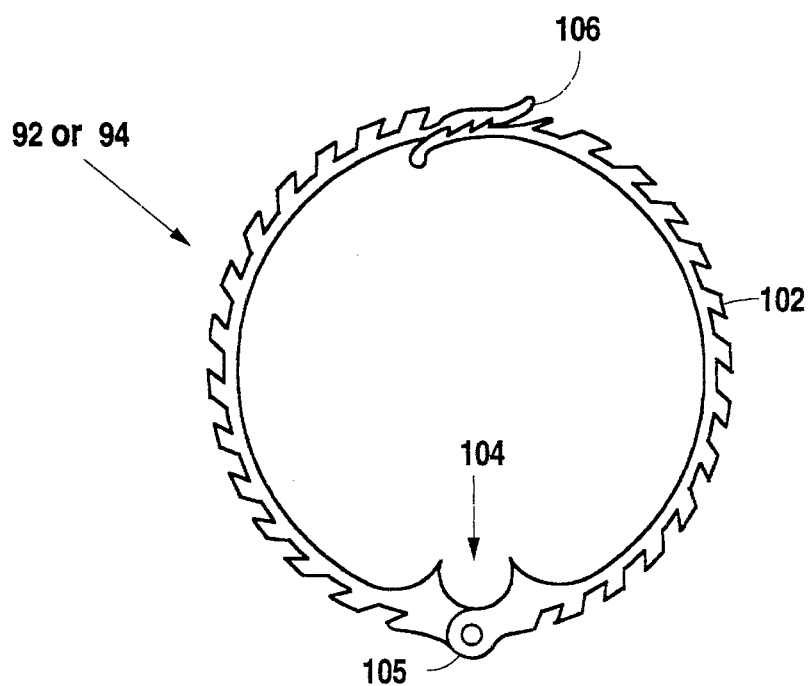
FIGS. 10a–c are side elevational views of the circular members of the bone alignment device of the present invention.
Figure 10B:
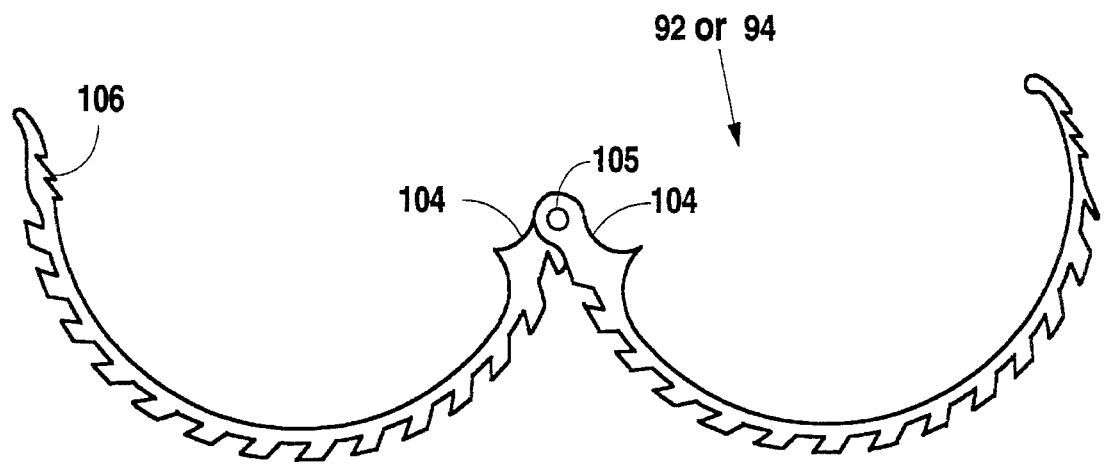
Figure 10C:
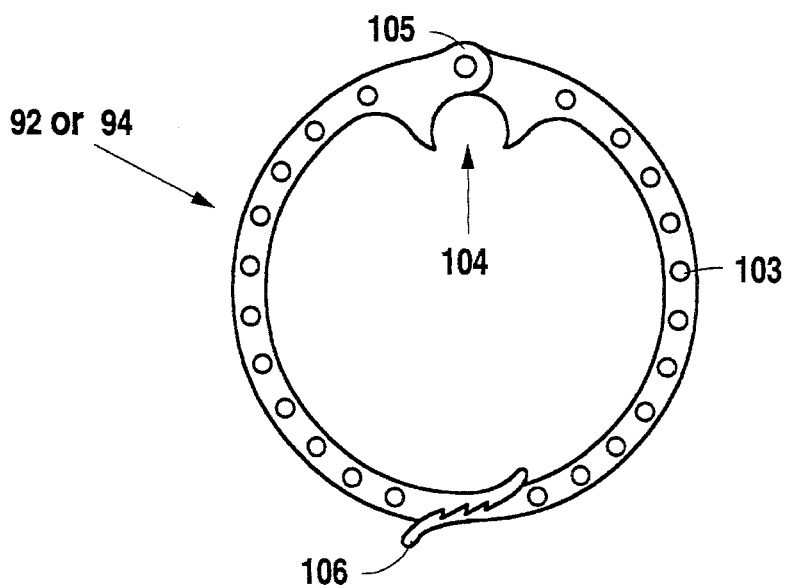

Referring to FIGS. 10a–c, the first (92) and the second (94) circular members are identical in structure and can have receiving means, such as angled teeth (102) on the outer circumference of the members (92) and (94). The angled teeth (102) are present to allow the first and the second ends of the longitudinally extending connectors to be secured, thus the first (92) and the second (94) circular members are connected using these angled teeth as receiving means. Another configuration of the circular member has circular openings as the receiving means located along the circumference of the members (92) and (94). Further each of the circular members is adapted to accept the tubular member (96) when the first (92) and the second (94) circular members are in a closed position. FIG. 10a shows a circular member in the closed position with the portion (104) of the circular member adapted to accept the tubular member (96) which is directly adjacent to a hinged means (105). The circular members can be closed by a closing means (106). FIG. 10b shows a circular member (92) or (94) in an open position. FIG. 10c shows a circular member (92) or (94) in the closed position with circular openings (103) rather than teeth. The figures show the preferred embodiments, but any configuration of a receiving means which allows the attachment of the tubular member (96) or connectors (98) to the circular members (92) and (94) is considered to be encompassed by the disclosed invention.

The tubular, longitudinally extending member (96) removably connects the first (92) and the second (94) circular members by fitting into the portion (104) of each of the circular members. The tubular member (96) may simply be a tube which cannot be adjusted which would make it necessary to have bone alignment devices of varying lengths to fit the many different lengths of the fractured bones of patients. However, the preferred embodiment is a telescoping tubular member so that the length of the tubular member can be adjusted to correspond to the length of the bone to be aligned. Referring to FIG. 9, when the tubular member (96) is adjustable as a result of telescoping pieces, the outer telescoping piece (108) is held in position over the inner telescoping piece (110) by a means (112) for holding the outer and inner telescoping pieces together at the desired length.

The longitudinally extending connectors (98) have a first end (116) and a second end (118), each removably attached to the first (92) and the second (94) circular members by a first (120) and a second (122) securing means which are adapted to fit between the angled teeth (102) or the circular openings (103) of the first (92) and the second (94) circular members. The bone alignment device (90) must have at least two longitudinally extending connectors (98) but it can have more than two connectors if more are required to align the fractured bone. The number of connectors present is only limited by the maximum number of connectors which could be attached to the first (92) and second (94) circular members and function to align the bone although it is unlikely that more than four to six connectors would be used to align and hold a fractured bone.

Figure 11:
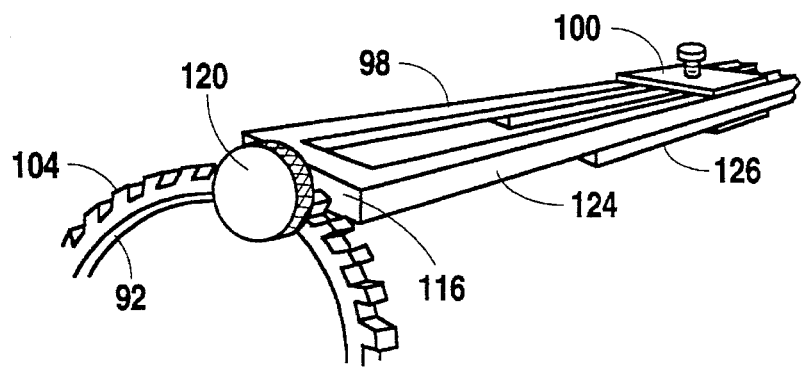
FIG. 11 is a perspective view of a partial circular member and a partial connector of the bone alignment device of the present invention.

In a preferred embodiment as shown in FIGS. 9 and 11, each of the connectors (98) are composed of two U-shaped arms extending longitudinally from each of the first (120) and the second (122) securing means. The first arm (124) and the second arm (126) of the connector (98) overlap and are removably secured in this overlapped position by at least one bone alignment means (100) on each connector (98).

Figure 12:
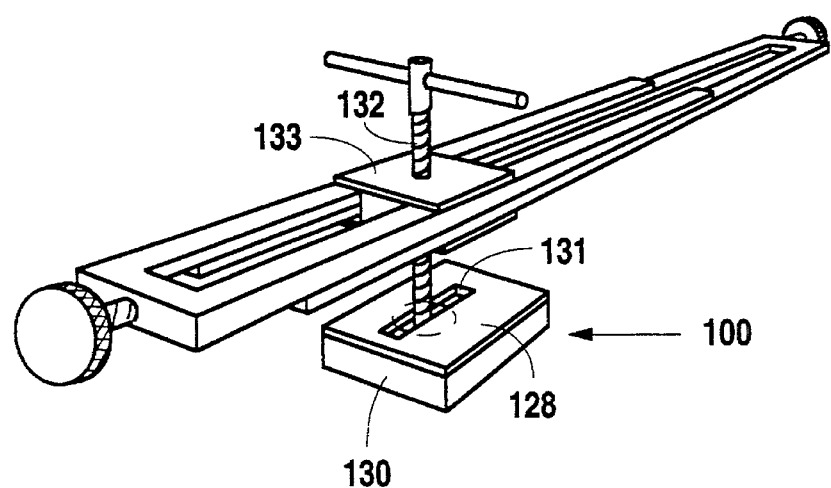
FIG. 12 is a perspective view of the connector of the bone alignment device of the present invention.

At least one adjustable bone alignment means (100) should be attached to each connector (98) of the bone alignment means (90). It may be necessary to attach two or three adjustable bone alignment means (100) to each connector (98) to align the fractured bone. Referring now to FIG. 12, the bone alignment means (100) comprises a flat base (128) having a pad (130) for applying pressure to the limb. The flat base (128) has a longitudinal slot (131) for receiving a threaded adjustment means (132) which is capable of moving the base (128) perpendicularly to the connector (98) for adjusting the amount of pressure exerted through the pad (130) on the limb. The pad (130) can be make of any material which is soft but firm in texture, such as felt, foam, etc. In a more preferred embodiment, the threaded adjustment means (132) passes through a H-shaped overlap securing means (133) which removably secures the U-shaped arms in an overlapped position.

Figure 13A:
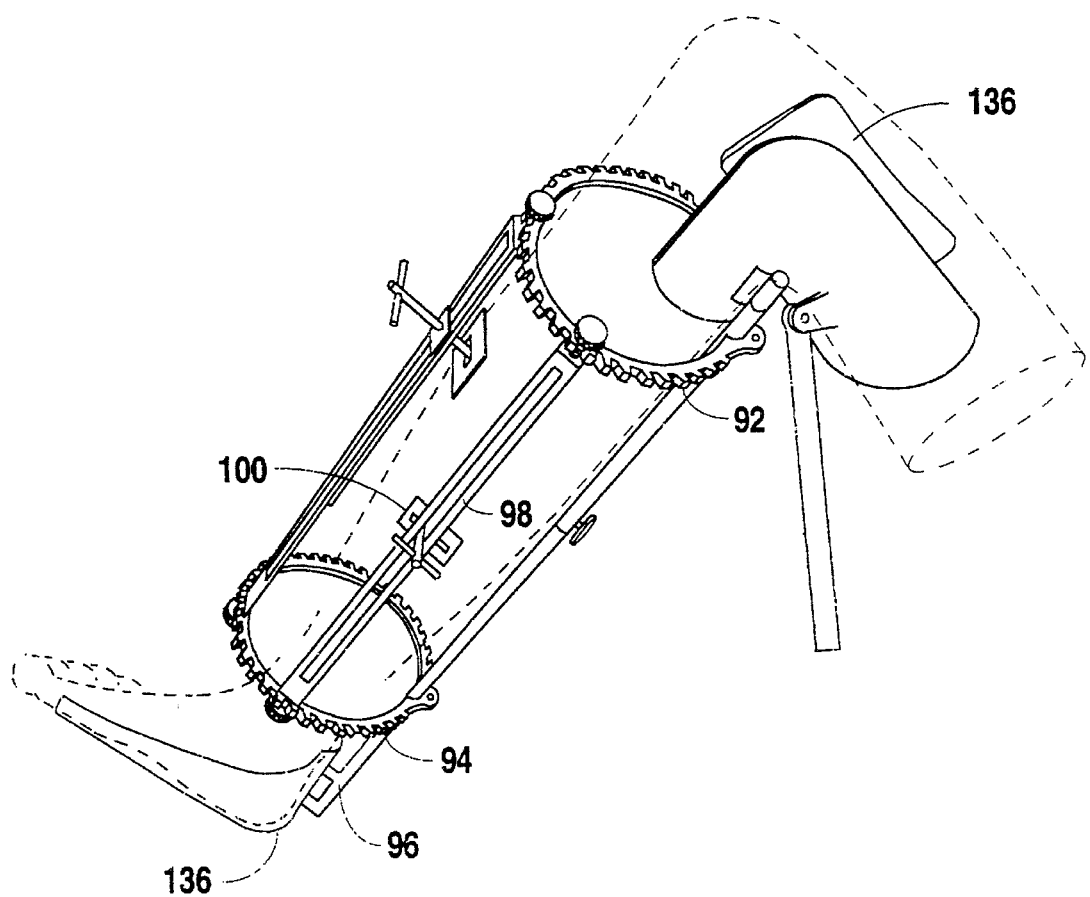
FIGS. 13a–c are perspective views of the bone alignment devices of the present invention as they would be used to hold a limb.
Figure 13B:
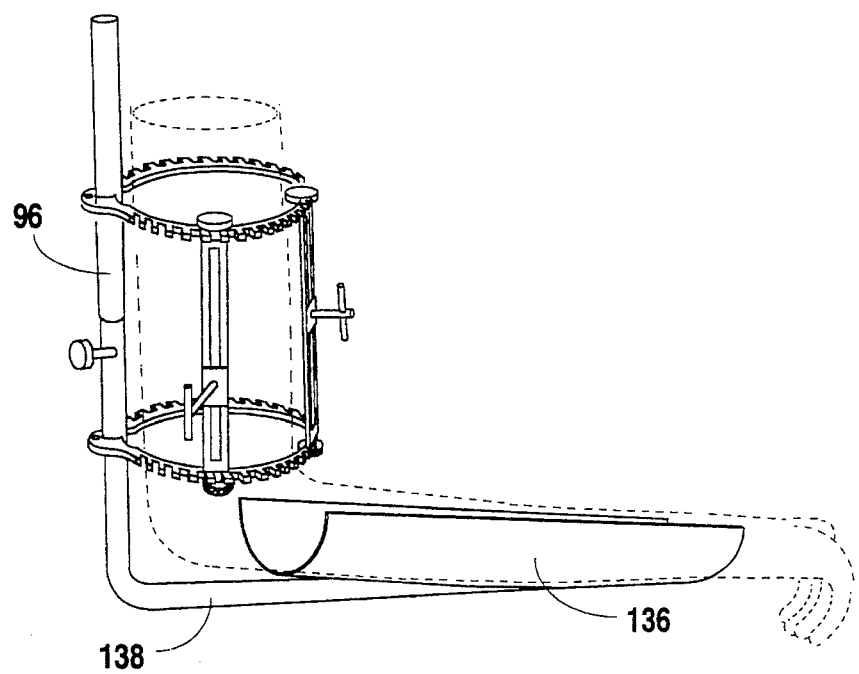
Figure 13C:
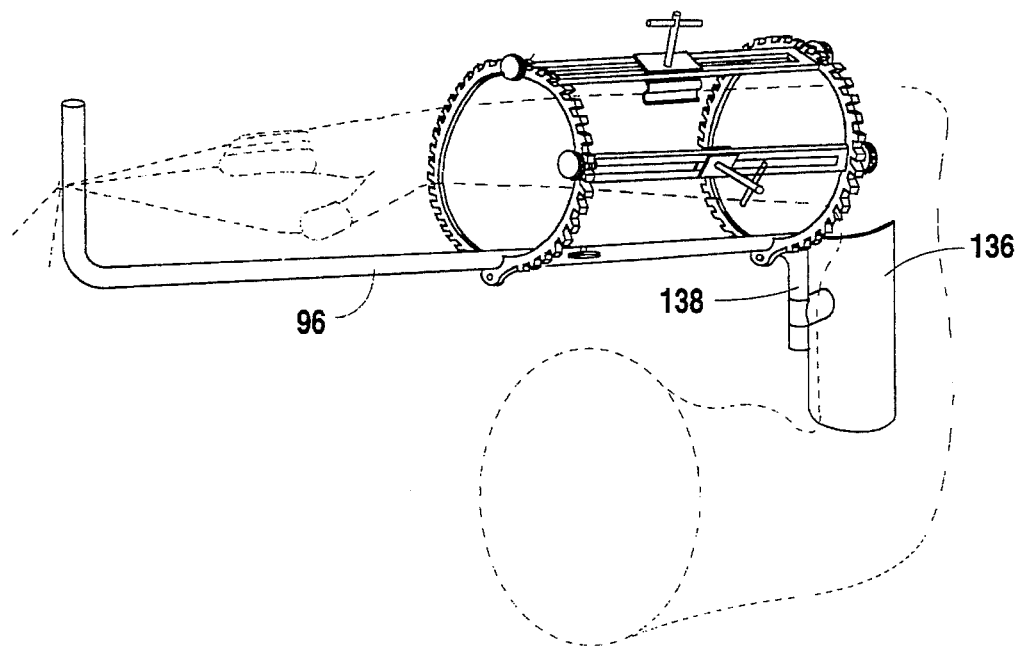
Figure 14A:
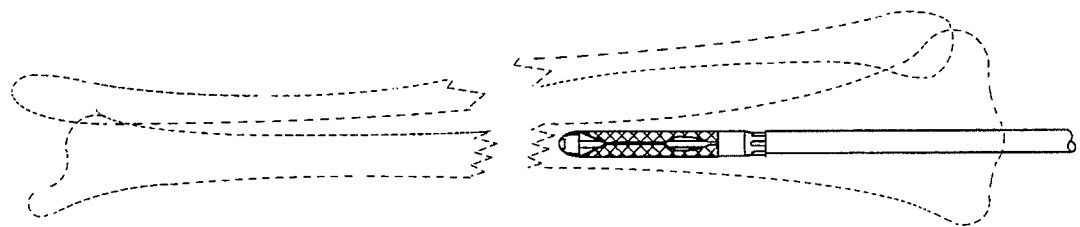
FIG. 14 is a side view of a broken fibula and tibia and the bone fixation device of the present invention showing the insertion of the device and the compression of the broken bone.
Figure 14B:
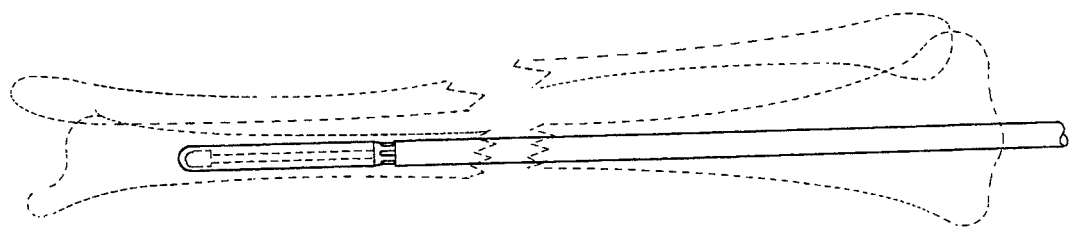
Figure 14C:
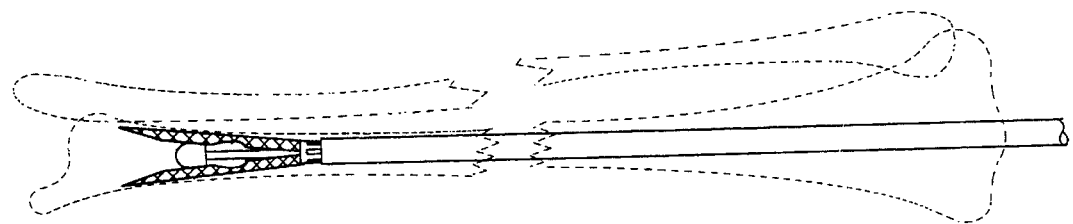
Figure 14D:
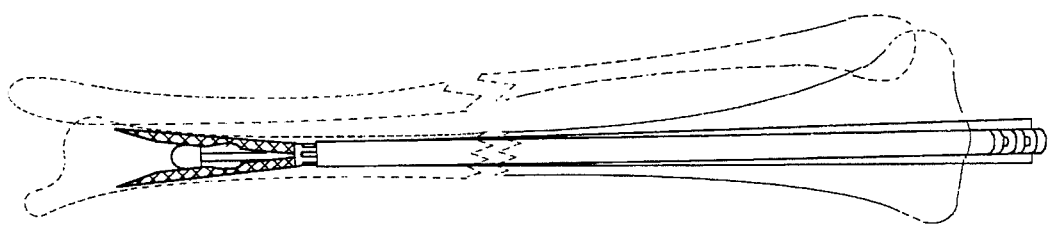
Figure 14E:
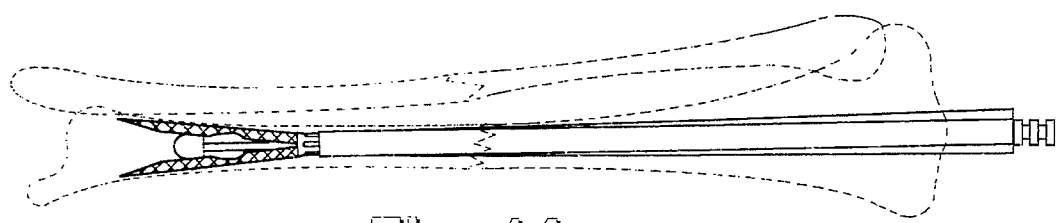

The bone alignment device (90) may additionally have attached to it a limb holder for holding the limb containing the fractured bone. FIGS. 13a–c provide examples of such adaptations of the present invention. The limb holder (136) is attached to the tubular member (96) at one of its ends as in FIG. 13a which shows a foot holder and leg holder. FIGS. 13b and 13c show that the limb holder (136) is attached to an extension (138) of the tubular member (96) at either of its ends.

The purpose of these limb holders (136) is to steady the limb for surgery and to counteract the traction which is put on the limb to aid in aligning the fractured bone. Additionally the bone alignment device (90) may be attached to a table in the operating room with a securing device and stabilizing rod which would attach to the tubular member (96) and/or the limb holder (136).

The present invention provides a system for fixing a fractured bone by using the combination of the bone fixation device and the bone alignment device. The following use of the bone fixation device (20) and the bone alignment device (90) will now be described. The patient is prepared for surgery. The bone alignment device (90) is attached to the limb of the patient containing the broken bone by applying light pressure with the several bone alignment means (100) to hold the bone alignment device (90) in place on the limb. The patient is then positioned to allow maximum use of the imaging apparatus, such as the fluoroscope, and then X-rays are taken to determine the size of the components of the bone fixation device (20) which should be inserted.

The fractured bone must now be aligned. The bone alignment means (100) which are attached to the connectors (98) of the bone alignment device (90) are adjusted to apply pressure to the patient's limb and by doing so move the bone so as to align it. After each adjustment with the various bone alignment means (100), X-rays are taken with the fluoroscope to monitor the progress of the alignment of the fractured bone.

After the fractured bone has been aligned, a small hole is made in one of the ends of the bone (now referred to as the proximal end of the bone) with an awl. This hole can be enlarged with a drill if necessary. The bone fixation device (20) is inserted into the proximal end of the fractured bone by hammering or tapping it in. The bone fixation device (20) which has been selected is an appropriate size compression device (22) engaged with an elongated member (24) for the length and size of the bone. The elongated member (24) is or preferably may be of a smaller diameter than is required for proper fixation of the fractured bone.

Referring now to FIGS. 14a–e, the bone fixation device (20) is inserted up to the point in the medullary canal prior to the fracture. The bone fixation device is tapped further into the medullary canal of the bone, past the fracture and to the distal end of the bone beyond the widening of the medullary canal. Once the bone fixation device (20) is in place, the compression wire (38) is pushed forward to release the compression blades (54) and the compression wire (38) is pulled back out of the proximal end of the bone thus sliding the head (48) via the prongs (50) of the compression wire (38) in the inner grooves (60). The compression wire (38) is protruding out of the proximal end of the bone to allow this manipulation by the surgeon. When the compression blades (54) open, they are compressed against the walls of the medullary cortex. When this compression is tight, further pulling of the wire will force the distal fragment of the fractured bone closer to the proximal fragment thus compressing the fracture in the bone.

After the fracture is stabilized, X-ray monitoring will allow the surgeon to determine whether the compression obtained is satisfactory. To obtain satisfactory compression for healing of the fractured, it may be necessary to change the entire bone fixation device by pushing the compression wire (38) forward and closing the blades (54) of the bone fixation device (20) and removing it from the bone. Or it may only be necessary to remove the elongated member (24) from the bone fixation device, leaving the compression device (22) in the bone until an elongated member (24) with a better fit has been selected. This is performed by disengaging the elongated member (24) from the compression device (22) at the fluted portions of each. In both cases, a satisfactory bone fixation device (20) or an elongated member (24) which provides a better fit is inserted into the medullary canal. The proper fit of the devices is determined by the surgeon using X-rays and the physical fit of the device in the bone. Once the appropriate device has been selected, the surgeon will determine whether it is necessary to further compress the fracture by adding one to four shims (74) to elongated member (24). If shims are added to the elongated member (24), the elongated member (24) should not be completely inserted into the bone until the shims (74) are in place.

Once the proper size of the bone fixation device (20) has been selected, any further compression of the fracture can be obtained by further pulling the compression wire (38) to its locking position. The device is locked by inserting a plate plus a clip at the proximal end of the bone. The wire is cut above this point and the incision is closed. After the fracture is mended, the bone fixation device (20) can be removed or left in the medullary canal of the bone.

The above description provides a method of using the bone fixation device (20) and the bone alignment device (90) together; however, the bone fixation device (20) could be used in combination with manual manipulations by the medical staff to align the bone. Likewise the bone alignment device (90) can be used with other bone fixation devices.

Although Applicant has described his invention in detail with regard to the preferred embodiments, the disclosure is not intended to limit the invention, but rather, it is intended to cover such alternatives, modifications and equivalents that may be included in the spirit and scope of the invention as herein disclosed.

I claim:

1. A bone fixation device for use in the fixation of a fractured bone having a cortex and a medullary canal comprising:
   a compression device adapted for removable engagement with an elongated member comprising:
      a hollow, elongated body comprising an outer surface with three contiguously connected, distinctly shaped portions positioned in a proximal to distal direction as follows: a first portion, a second portion and a third slotted portion;
      a flexible, compression wire insertable through said body from the end of said first portion comprising a head located at the distal end of said compression wire and two laterally located prongs extending longitudinally from said head;
      at least two compression blades, each of said blades having an inner surface and an outer surface, and each of said blades having an arc-shape with a tip at the distal end of said blade and an arm at the proximal end of said blade, wherein said arm is engaged with one of said slots on said third portion of said body, and said blade further comprising an inner groove extending longitudinally on the inner surface of said blade wherein said inner groove is engaged with one of said laterally located prongs on said head allowing said compression wire to slide along said inner groove of said blade; and
      a hollow cylinder having an inner surface which is engaged with said second portion of said body securing said arms of said blades into said slots on said third portion of said body; and
   a hollow, elongated, curved member wherein the inner surface of said member is engaged with said compression device; and
   wherein the proximal end of said compression wire which is extending beyond the proximal end of said compression device is inserted through said elongated member and said elongated member is removably connected to said compression device by engaging said first portion of said body of said compression device with the distal portion of said inner surface of said elongated member.

2. The device according to claim 1, wherein said outer surface of said compression blade is rough and ridged for functional engagement with said medullary canal.

3. The device according to claim 1, wherein the outer surface of said elongated member is square-shaped.

4. The device according to claim 3, wherein the outer surface of each of the sides of said elongated member further comprises a pair of longitudinally extending parallel grooves.

5. The device according to claim 4, further comprising at least one longitudinally extending shim, having a distal and a proximal end, wherein said shim has a flat base which slides inside said pair of longitudinally extending parallel grooves on said outer surface of said side of said elongated member.

6. The device according to claim 5, wherein said shim is wedge-shaped for a portion of the distal end.

7. A fractured bone alignment device for use in the fixation of a fractured bone wherein said device is placed on the limb of an individual wherein said limb contains said fractured bone, wherein said device comprises:
   a first and a second adjustable, circular member having receiving means along the circumference of said members wherein each of said circular members accepts a tubular member;
   a tubular, longitudinally extending member wherein said tubular member removably connects said first and said second circular members; and
   at least two longitudinally extending connectors having a first and a second end each removably attached to said first and said second circular members by a first and a second securing means which fit into the receiving means of said first and said second circular members; and
   at least one adjustable bone alignment means attached to each of said connectors for applying pressure to said limb, wherein said bone alignment means comprises a flat base having a pad for applying said pressure and having a longitudinal slot for receiving a threaded adjustment means capable of moving said base perpendicularly to said connector for adjusting the amount of pressure exerted through said pad on said limb.

8. The device according to claim 7, wherein said connector further comprises two arms longitudinally extending from each of said first and second securing means, said first arm and said second arm of said connector overlapping and removably secured in said overlapped position by said bone alignment means.

9. The device according to claim 8, wherein said threaded adjustment means passes through an H-shaped overlap securing means which removably secures said arms in said overlapped position.

10. The device according to claim 9, wherein said longitudinally extending arms are U-shaped.

11. The device according to claim 7, wherein said tubular, longitudinally extending member is a telescoping member.

12. An apparatus for use in the fixation of a fractured bone having a cortex and a medullary canal, wherein a fractured bone alignment device is placed on a limb containing the fractured bone to align the fractured bone and a bone fixation device is used to fix said fractured bone, wherein said fractured bone alignment device comprises:
   a first and a second adjustable, circular member having receiving means along the circumference of said members wherein each of said circular members accepts a tubular member;
   a tubular, longitudinally extending member wherein said tubular member connects said first and said second circular members; and
   at least two longitudinally extending connectors having a first and a second end each removably attached to said first and said second circular members by a first and a second securing means which are adapted to fit into the receiving means of said first and said second circular members; and
   at least one adjustable bone alignment means attached to each of said connectors for applying pressure to said limb; and wherein said bone fixation device comprises:

a compression device adapted for removable engagement with an elongated member comprising:
- a hollow, elongated body further comprising an outer surface with three contiguously connected, distinctly shaped portions positioned in a proximal to distal direction as follows: a first portion, a second portion and a third slotted portion;
- a flexible, compression wire insertable through said body from the end of said first portion further comprising a head located at the distal end of said compression wire and two laterally located prongs extending longitudinally from said head;
- at least two compression blades, each of said blades having an inner surface and an outer surface, and each of said blades having an arc-shape with a tip at the distal end of said blade and an arm at the proximal end of said blade, wherein said arm is engaged with one of said slots on said third portion of said body, and said blade further comprising an inner groove extending longitudinally on the inner surface of said blade wherein said inner groove is engaged with one of said laterally located prongs on said head allowing said compression wire to slide along said inner groove of said blade; and
- a hollow cylinder having an inner surface which is engaged with said second portion of said body securing said arms of said blades into said slots on said third portion of said body; and
- a hollow, elongated, curved member wherein the inner surface of said member is engaged with said compression device;

wherein the proximal end of said compression wire which is extending beyond the proximal end of said compression device is inserted through said elongated member and said elongated member is removably connected to said compression device by engaging said first portion of said body of said compression device with the distal portion of said inner surface of said elongated member.

13. The apparatus according to claim 12, wherein said connector of said bone alignment device further comprises two arms longitudinally extending from each of said first and second securing means, said first arm and said second arm of said connector overlapping and removably secured in said overlapped position by said bone alignment means.

14. The apparatus according to claim 13, wherein said bone alignment means comprises: a flat base having a pad for applying pressure to said limb, said flat base having a longitudinal slot for receiving a threaded adjustment means capable of moving said base perpendicularly to said connector for adjusting the amount of pressure exerted through said pad on said limb.

15. The apparatus according to claim 14, wherein said threaded adjustment means passes through an H-shaped overlap securing means which removably secures said arms in said overlap position.

16. The apparatus according to claim 15, wherein said longitudinally extending arms are U-shaped.

17. The apparatus according to claim 12, wherein said tubular, longitudinally extending member is a telescoping member.

18. The apparatus according to claim 12, wherein said outer surface of said compression blade is rough and ridged for functional engagement with said medullary canal.

19. The apparatus according to claim 12, wherein the outer surface of said elongated member is square-shaped.

20. The apparatus according to claim 19, wherein the outer surface of each of the sides of said elongated member further comprises a pair of longitudinally extending parallel grooves.

21. The apparatus according to claim 20, further comprising at least one longitudinally extending shim, having a distal and a proximal end, wherein said shim has a flat base which slides inside said pair of longitudinally extending parallel grooves on said outer surface of said side of said elongated member.

22. The device according to claim 21, wherein said shim is wedge-shaped for a portion of the distal end.

\* \* \* \* \*